United States Patent [19]

Findl

[11] Patent Number: 4,850,959

[45] Date of Patent: Jul. 25, 1989

[54] BIOELECTROCHEMICAL MODULATION OF BIOLOGICAL FUNCTIONS USING RESONANT/NON-RESONANT FIELDS SYNERGISTICALLY

[75] Inventor: Eugene Findl, Murrieta Hot Springs, Calif.

[73] Assignee: Bioresearch, Inc., Farmingdale, N.Y.

[21] Appl. No.: 227,296

[22] Filed: Aug. 2, 1988

[51] Int. Cl.$^4$ ............................................. A61B 17/52
[52] U.S. Cl. ...................................................... 600/14
[58] Field of Search ...................... 600/1, 2, 13, 14, 15, 600/9

[56] References Cited

U.S. PATENT DOCUMENTS 4,428,366  1/1984  Findl et al. ............................. 600/14

OTHER PUBLICATIONS

Biomedical Ultrasonics, P. N. T. Wells, Academic Press, New York 1977 pp. 423–424.

Primary Examiner—Francis Jaworski
Assistant Examiner—Scott M. Getzow
Attorney, Agent, or Firm—Larson and Taylor

[57] ABSTRACT

A method of controlling cellular influx and efflux of ionic calcium to modulate the functioning of biological entities comprising subjecting such entities to both resonant and non-resonant fields. Representative of the synergistic application of these two types of fields in their use in controlling blood glucose levels in living animals afflicted with hyperglycemia. This method comprising subjecting at least the liver and pancreas area of an animal having a blood glucose level of at least 180 mg/dL to a resonant electromagnetic field applied post-prandially until the animal's blood glucose level is reduced to about 150 mg/dL then stopping application of said resonant frequency electromagnetic field and subjecting said animal to a non-resonant frequency electromagnetic field to further reduce the animal's blood glucose level.

17 Claims, 7 Drawing Sheets

BIOELECTROCHEMICAL MODULATION OF BIOLOGICAL FUNCTIONS USING RESONANT/NON-RESONANT FIELDS SYNERGISTICALLY

BACKGROUND OF THE INVENTION

This invention relates to non-invasive methods for controlling cellular ionic calcium levels. More particularly, the invention describes methods for reducing or increasing blood glucose levels in living animals, including man, by cytosolic ionic calcium level control, through the application of low energy electromagnetic, electric, magnetic and ultrasonic fields.

Hyperglycemia, or as it is more commonly known, diabetes, is primarily characterized by abnormally high concentration levels of blood glucose, both under fasting and non-fasting conditions. In Type I diabetes, the abnormal glucose levels are principally due to an insufficiency of pancreatic beta cell produced insulin. Insulin is required for the rapid transfer of glucose from the blood to most cells of the body. Low insulin levels result in glucose remaining in the blood for extended time periods, leading to hyperglycemia and its complications. In Type II diabetes, sometimes called adult or obesity onset diabetes, sufficient insulin is present but glucose levels remain high for reasons as yet not generally agreed upon but believed to be due to liver/pancreas dysfunctioning.

Most of the emphasis in diabetes research to find a cure for the disease has been placed on insulin as the "star" player in the control of hyperglycemia, particularly in the case of Type I diabetes. Glucagon and somatostatin, on the other hand, seems to have been placed in secondary role in both types of diabetes. Yet, glucagon and somatostatin are key players in both types, particularly so, since glucagon is the counter control to insulin and is essential to the action of the liver controlled release of glucose. Somatostatin, on the other hand, regulates the release of both insulin and glucagon. Both of these hormones are produced in the pancreas by alpha cells and delta cells respectively.

Hypoglycemia, or low blood sugar, is the converse of diabetes. Its symptoms are primarily characterized by blood glucose levels significantly below normal prior to food ingestion. However, dysfunctioning of the pancreas and/or liver, can lead to low levels of blood glucose, which in turn can produce symptoms of lethargy, cause fainting, etc.

The use of low energy electromagnetic fields to alleviate the hyperglycemia condition has been reported in the medical and patent literature. Documented therein, are the inconsistencies and indeed opposite results often reported by researchers using electromagnetic fields indicating that whether or not an electromagnetic field will effect a change in blood glucose levels seems to depend upon field parameters. For example, W. B. Jolley et al, "Magnetic Field Effects on Calcium Efflux and Insulin Secretion in Isolated Islets of Langerhans", Bioelectromagnetics, 4, 103–106, (1983), presented data illustrating that insulin secretion of pancreatic beta cells was reduced under the influence of pulsed electromagnetic fields (200 microsecond pulses at a 4 KHertz rate with a burst duration of 4 milliseconds and a repetition rate of 15 pulses per second). Such a decrease in insulin secretion would be expected to increase blood glucose levels. On the other hand, Milch et al., "Electromagnetic Stimulation of the Rat Pancreas and the Lowering of Serum Glucose Levels", Trans. Am. Soc. Artif. Intern. Organs, 27, 246 (1981) presented data showing that blood glucose levels of chemically induced Type I diabetic rats was decreased by a very specific electromagnetic field (350 microsecond pulses at a 15 Hz repetition rate). The data presented by Findl et al. in U.S. Pat. No. 4,428,366 illustrates the finding of Milch et al.

While not agreeing on the mechanisms involved, many of the leading researchers in the field of Bioelectrochemistry/Biomagnetics agree that exogenous, i.e., externally applied, fields modify cellular calcium ion transport. A. Chiabrera et al, "Interaction Between Electromagnetic Fields and Cells: Microelectrophonetic Effects of Ligands and Surface Receptors", Bioelectromagnetics, 5, 173, (1984), in discussing their membrane receptor model of electric field/cell interactions state that they "adhere to the working hypothesis that when two or more receptors encounter each other, they form an encounter complex which appears to enhance calcium ion influx", if an endogenous or exogenous electric field is present. A. R. Liboff, "Cyclotron Resonance in Membrane Transport", in "Interactions Between Electromagnetic Fields and Cells", 281, Plenum Press, (1985), on the other hand, indicates exogenous fields cause a resonant energy transfer to potassium ion influx, which in turn causes increased calcium ion efflux via a potassium/calcium ion transmembrane exchange. S. M. Bawin et al., "Effects of Modulated VHF Fields on the Central Nervous System", Ann NY Acad. Sci., 247, 74, (1975) and "Sensitivity of Calcium Binding in Cerebral Tissue to Weak Environmental Electric Fields Oscillating at Low Frequency", Proc. Nat'l. Acad. Sci., U.S.A., 73, 1999 (1976), have experimentally verified that calcium-ion efflux from the external bilipid layers of chick cerebral hemisphere can be either enhanced or diminished, depending upon stimulation frequency, energy level and the type of stimulation, i.e., modulated RF or sinusoidal AC. E. Neumann, "Membranes and Electromagnetic Fields", 1, Abstracts, 8th Ann. Bioelectromagnetics Soc. Mtg., Madison, June (1986), states that regions adjacent to membrance surfaces are the targets of electric field effects, altering ionic diffusion. In particular, calcium ion influx is caused by an increased concentration gradient on the external bilayer due to field-membrane interactions. E. Findl, "Membrane Transduction of Low Energy Level Fields and the Ca++ Hypothesis" in "Mechanistic Approaches to Interactions of Electric and Electromagnetic Fields with Living Systems", 15–33, Plenum Pub. (1987), describes why some investigators experimentally show electromagnetic fields causing calcium ion efflux from cellular cytosols, while others show exogenous fields cause calcium influx. Basically both cytosolic influx and influx can occur. The direction of calcium flow is principally dependent upon field frequency. Certain specific frequencies (resonant frequencies) cause calcium ion influx, while other, non-resonant frequencies cause calcium ion efflux. The frequency dependence factor is the key to the control of cytosolic calcium levels and modification of functioning. By increasing or decreasing ionized cytosolic calcium levels, certain cellular functions, such as secretion of the pancreatic hormones insulin, glucagon and somatostatin, can be modulated.

The various electromagnetic fields heretofore employed by researchers has included what can be referred to as "resonant frequency electromagnetic fields" and "non-resonant frequency electromagnetic fields". By "resonant frequency electromagnetic fields", as used in the specification and appended claims, is meant any waveform, having a fundamental or modulation frequency of 15 Hertz or an odd multiple thereof, up to about the 19th harmonic, i.e., about 285 Hertz. By the term "non-resonant frequency electromagnetic fields" as used herein and the appended claims is meant any waveform, electromagnetic, electric, magnetic or ultrasonic field of any frequency (other than 15 Hertz or its odd multiples) between 0.1 and 10 KHertz. While researchers have heretofore employed both forms, i.e., the resonant and non-resonant frequency electromagnetic fields individually in attempts to control cytosolic ionic calcium levels and affect blood glucose levels, the use of either of these electromagnetic fields alone has provided less than satisfactory control of these levels.

Although emphasis has been placed herein on the use of low frequency electromagnetic fields, it should be understood that pulsed or alternating electric fields, amplitude modulated radio frequency fields and amplitude modulated ultrasonic vibrations can be used to similarly affect calcium ion cellular transport. Electric fields can be applied by direct contact of electrodes to the animal's skin or by capacitive coupling. Radio frequencies suitably amplitude modulated at resonant or non-resonant frequencies can be applied by the use of suitable antennas. Similarly, mechanically moved magnets, vibrated or otherwise caused to move at resonant or non-resonant frequencies can be used. Ultrasonic fields induce electrokinetic streaming potentials and streaming currents in living tissue and thus, when pulsed or modulated at resonant o non-resonant frequencies can also be employed.

A wide range of field strengths have been described in the technical literature to modulate calcium ion transport in biological tissue. Magnetic fields, for example, have been successfully employed from the milligauss to kilogauss range. Electric fields have ranged from microvolt/centimeter to volts/centimeter. The most effective range for fields strength appears to be in the 0.1 to 100 gauss and 0.01–10 volt/centimeter range.

SUMMARY OF THE INVENTION

It has now been discovered that use of the combination of a resonant frequency field and a non-resonant frequency field, each applied at appropriate times, permits control of a number of biological functions, such as blood glucose levels, not achievable by use of either field alone.

Moreover, use of resonant/non-resonant frequency fields in accordance with the invention provides the necessary cellular ionized calcium level controls without the need of chemical or pharmaceutical additives, but, in fact, such additives can enhance the effects of electromagnetic fields.

For example, in accordance with the method of the invention, blood glucose levels in living animals afflicted with Type II hyperglycemia are controlled by subjecting the liver and pancreas area of an animal having a fasting blood glucose level of greater than 180 mg/dL to a resonant electromagnetic field applied post-prandially until the animal's fasting blood glucose level is reduced to about 150 mg/dL, then stopping application of said resonant frequency electromagnetic field and subjecting said animal to a non-resonant frequency electromagnetic field to further reduce the animal's fasting blood glucose level to a normal blood glucose level.

It is to be understood that the invention is not necessarily a cure for diabetes. The invention does significantly reduce the need for drugs or insulin injections as, for instance, in Type I hyperglycemia. Basically, it provides a means to assist the body to activate normal pancreas and liver cellular functions to control cytosolic ionized calcium levels and thus glucose levels. Once normal blood glucose levels are reached, application of treatment according to the method of the invention may be occasionally required to maintain them.

In another aspect of the invention, blood glucose levels in living animals afflicted with hyporglycemia are controlled by subjecting at least the liver/pancreas area of an animal having a fast blood sugar level less than 80 mg/dL to a non-resonant electromagnetic field applied pre-prandially (before meals) on a daily basis until the animal's blood glucose level is increaed to between 80 and 120 mg/dL.

The critical or essential factors in the method of the invention involve the particular frequency employed, the timing of the field application and in the case of diabetes, the blood glucose level of the patient at the time of treatment by the electromagnetic field. For example, it has been found that a resonant frequency electromagnetic field, if applied at the proper time, reduces glucose levels. On the other hand, application of the same resonant frequency electromagnetic field at the wrong time has been found to increase blood glucose levels. Similarly, a non-resonant frequency electromagnetic field applied at the proper time, reduces blood glucose levels and if applied at the wrong time increases blood glucose levels.

More specifically, experimentation has determined that the application post-prandially (after meals) of resonant frequency electromagnetic fields to animals having high fasting blood glucose levels, i.e., above 180 mg/dL can reduce the blood glucose level but their application at lower levels, below 160 mg/dL tends to have the opposite effect, that is to increase blood glucose levels. Application post-prandially of non-resonant frequency electromagnetic fields, in contrast, has been found to reduce blood glucose levels, when fasting blood glucose levels are below about 160 mg/dL.

Another critical feature of the invention resides in the discovery that in order to obtain reductions in blood glucose content with either resonant or non-resonant electromagnetic fields, it is essential that the fields be applied post-prandially. Pre-prandial stimulation with either resonant or non-resonant frequency electromagnetic fields has been found to elevate blood glucose levels.

The electromagnetic fields of the invention are generated by supplying electric power from a suitable electric power supply means to an electromagnet such as a pair of Helmholtz type coils. The power supply means can comprise any one of a number of frequency generators having an adjustable output frequency. Thus, the power supply means provides a wave of power, pulsed or non-pulsed, to the electromagnet in which the frequency, shape and amplitude can be adjusted. The electric power supply means directs power to the electromagnet to provide a suitable magnetic strength of 0.1 to 100 gauss, preferably 1–30 gauss.

As aforementioned, the resonant frequency electromagnetic field of the invention has a frequency of 15 Hertz or an odd multiple thereof up to the 19th harmonic, i.e., about 285 Hertz. The preferred frequency is about 15 Hz, plus or minus 0.5 Hz.

The non-resonant field of the invention can be any frequency (other than 15 Hertz or its odd multiple) between 0.1 and 10K Hertz. The amplitude of both resonant and non-resonant fields are preferably in the 1–30 gauss range.

When employing resonant frequency fields, application of the field is timed to occur approximately 1.5 hours after eating. This corresponds to the time it takes for the patient's blood glucose level to reach peak levels post-prandially. Fields are applied for periods of time ranging from 0.5 to 2 hours, preferably 1 hour.

When employing non-resonant frequency fields, application of the field is timed to start immediately upon completion of a meal. Fields are applied for periods ranging between 0.5 and 1.5 hours, preferably 1.25 hours.

While reductions in blood glucose levels may be observed after only a short period of treatment according to the invention, several months of regular daily treatments after each meal will ordinarily be required to reduce and stabilize the blood glucose content to normal or near normal levels.

The biochemical mechanisms by which the present invention accomplishes the reduction of blood glucose levels is not fully known, but there is evidence indicating that electromagnetic fields interact with both the liver and pancreas (alpha, beta and delta cells). Briefly, it is believed that resonant frequency electromagnetic fields applied about 1.5 hours post-prandially for 1 hour, primarily cause an influx of calcium ions into the cytosol of beta cells, which results in an increased release of insulin. Non-resonant frequency electromagnetic fields, applied immediately post-prandially for 1.25 hours, on the other hand, primarily cause an efflux of calcium ion from hepatocytes (liver cells), thereby stimulating the liver to convert blood glucose to glycogen for storage, thereby further reducing blood glucose levels.

The invention and objects and advantages thereof will be described below in more detail with reference to the following drawings.

DETAILED DESCRIPTION OF THE PREFERRED EMBODIMENTS

Figure 1:
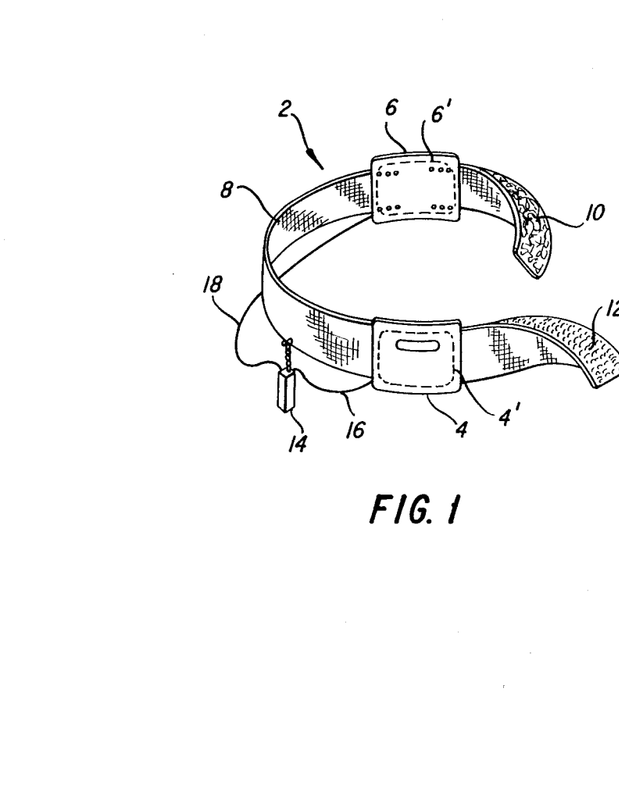
FIG. 1 is a perspective view of an electromagnet, powered by a rechargeable battery, that is used to generate the electromagnetic fields of the present invention.
Figure 2A:
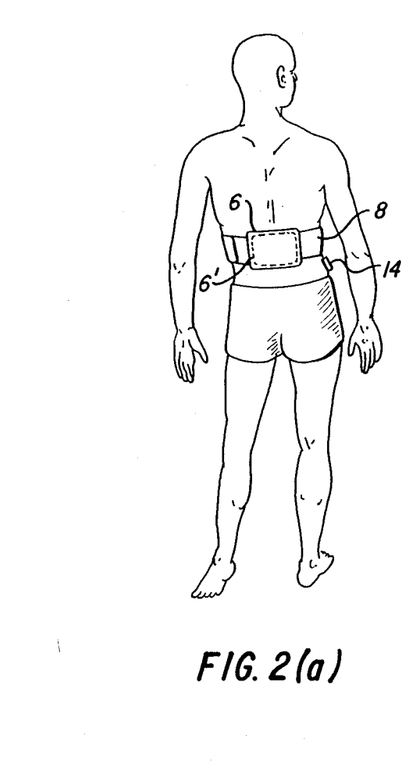
FIGS. 2(a) and 2(b) are front and rear views of a patient showing the position of the electromagnet when used for blood glucose level control.
Figure 2B:
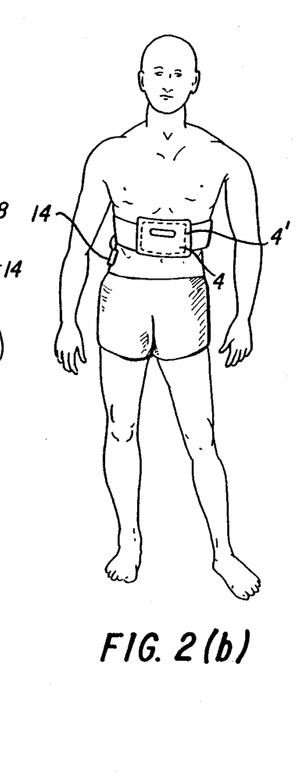
Figure 3:
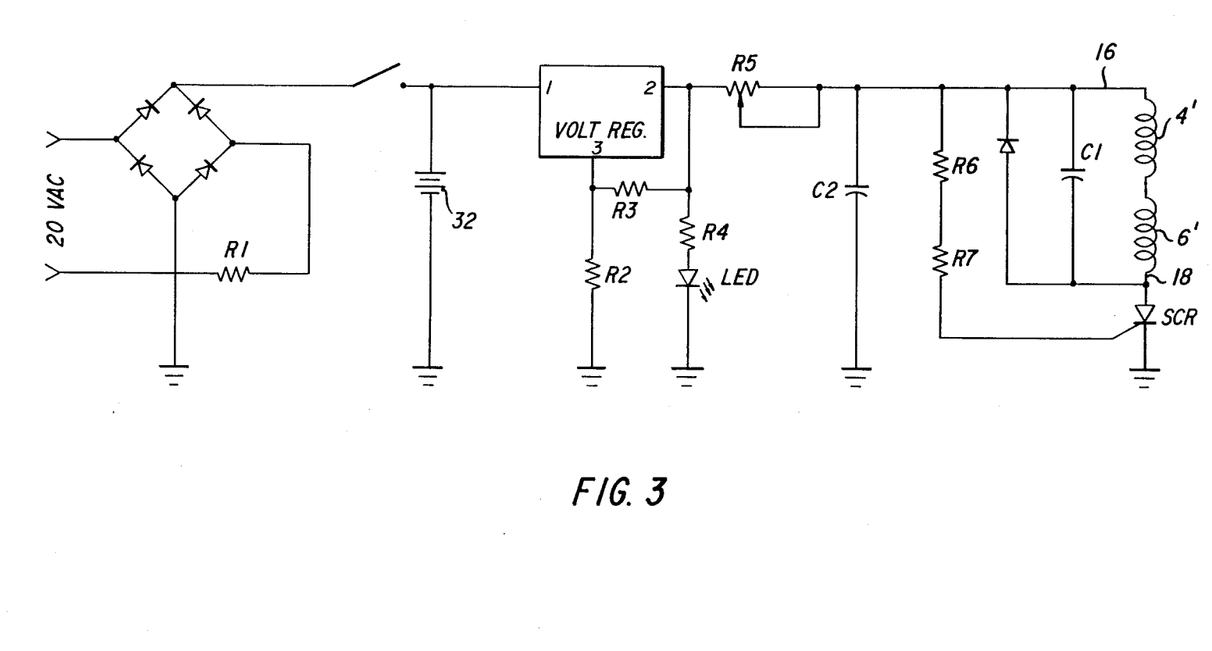
FIG. 3 is a schematic electrical diagram of a rechargeable, battery-operated, portable electromagnetic field generator used in the device shown in FIG. 1.

With reference now to the figures where like numerals represent like elements throughout the view, FIG. 1 depicts a field coil element designated 2 of the so-called Helmholtz configuration designed to enhance the strength of the electromagnetic field that traverses tissue positioned in-between. Field coil element 2 comprises front and back buckles 4 and 6 which house field coils 4' and 6', respectively. As is well known, Helmholtz type field coil electromagnets produce a substantially uniform magnetic field between the two coils and throughout radial slices therebetween. As shown in the figures, the coils are flat, rectangular coils, preferably having an equal number of turns and equal dimensions. Magnet wire (#30) is typically used to make the coils, each coil having a resistance of about 87 ohms. Coils 4' and 6' are arranged in a field coil element 2 so as to have a common axis (i.e., are coaxial) and are connected in series to a signal generator 14. A belt 8 passes through buckles 4 and 6. The ends of belt 8 are provided with loop means 10 and hook means 12 of the Velcro type for securing the field coil to the midriff or abdomen of the patient directly over the patients liver and pancreas as shown in FIG. 2(a) and FIG. 2(b). A signal generator 14 is attached to the coil 4' by means of wire 16 and to coil 6' by means of wire 18. A schematic electrical diagram of signal generator 14 used to produce a pulsed field is shown in FIG. 3. Basically, this unit is a rechargeable, battery-operated, portable electromagnetic field generator that uses two rechargeable 9 volt nickel/cadmium batteries 32 to provide field power. The frequency is adjustable over a range of approximately 10 to 50 Hz by varying the resistance $R_2$ and the size of capacitor $C_2$. Hence, by simple adjustment, the same unit can be used to generate both the resonant and non-resonant electromagnetic fields of the invention.

Figure 4:
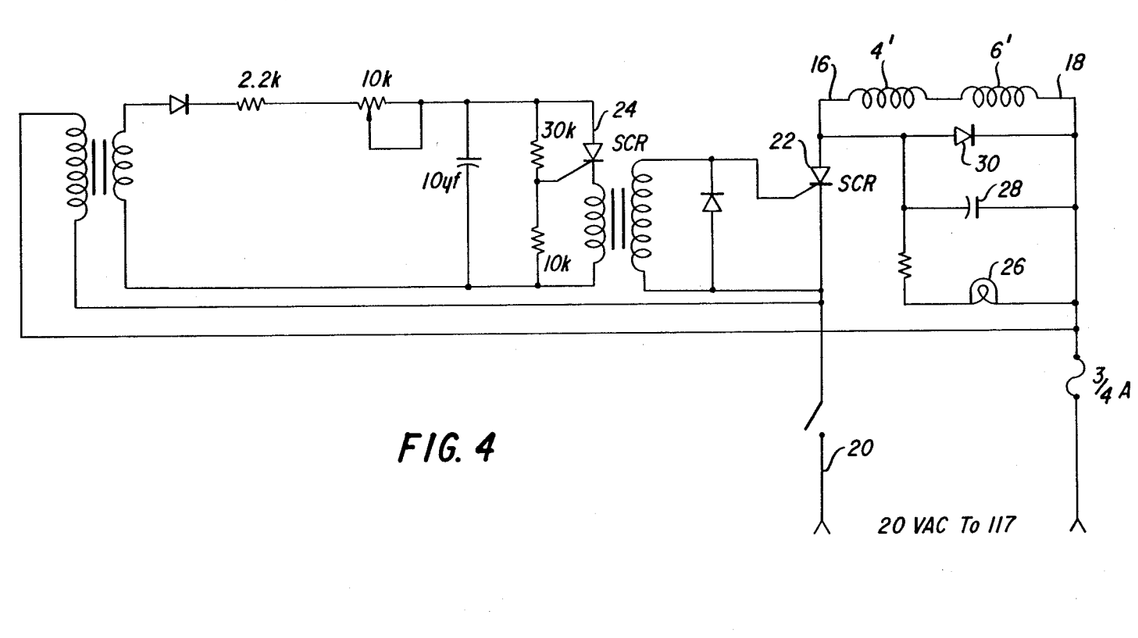
FIG. 4 is a schematic electrical diagram showing an embodiment of the invention using an AC current to generate the electromagnetic fields.

Alternatively, an AC powered device such as is shown schematically in the diagram of FIG. 4 can be used to generate a 15 Hz electromagnetic field. This device utilizes 20–117VAC, 60 Hz power 20 from a transformer or an AC outlet (not shown) to trigger a pair of silicon controlled rectifiers 22 and 24 to conduct once every fourth cycle of the line frequency. When the main SCR 22 conducts, supply voltage is applied across the field coils 4' and 6' until the line voltage reverses polarity, turning off the main SCR. A neon light 26 is provided across main SCR 22 to visually show that the field generating unit is operating. In addition, a 5 microfarad capacitor 28 and a diode 30 are placed across the field coils 4' and 6' to improve pulse shape.

Figure 5:
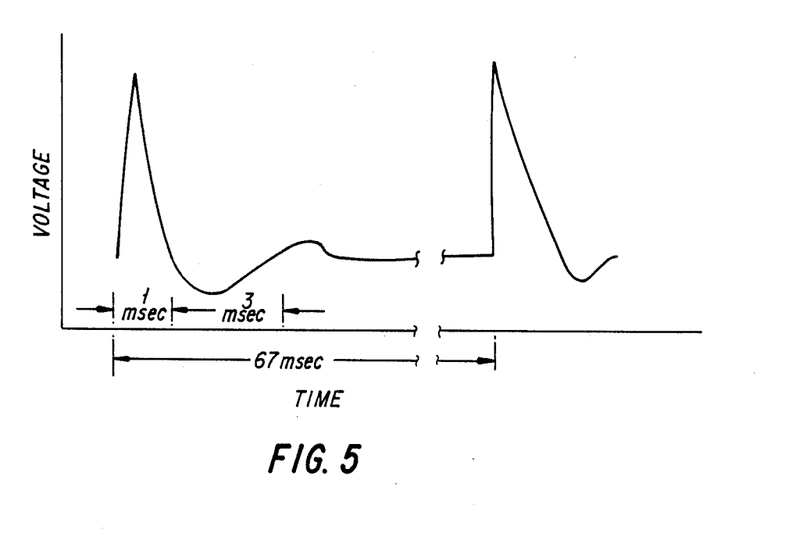
FIG. 5 is a typical on/off pulse generated by the field generators of FIGS. 3 and 4.

A typical 15 Hz on/off pulse to the field coils is shown in FIG. 5.

Figure 8:
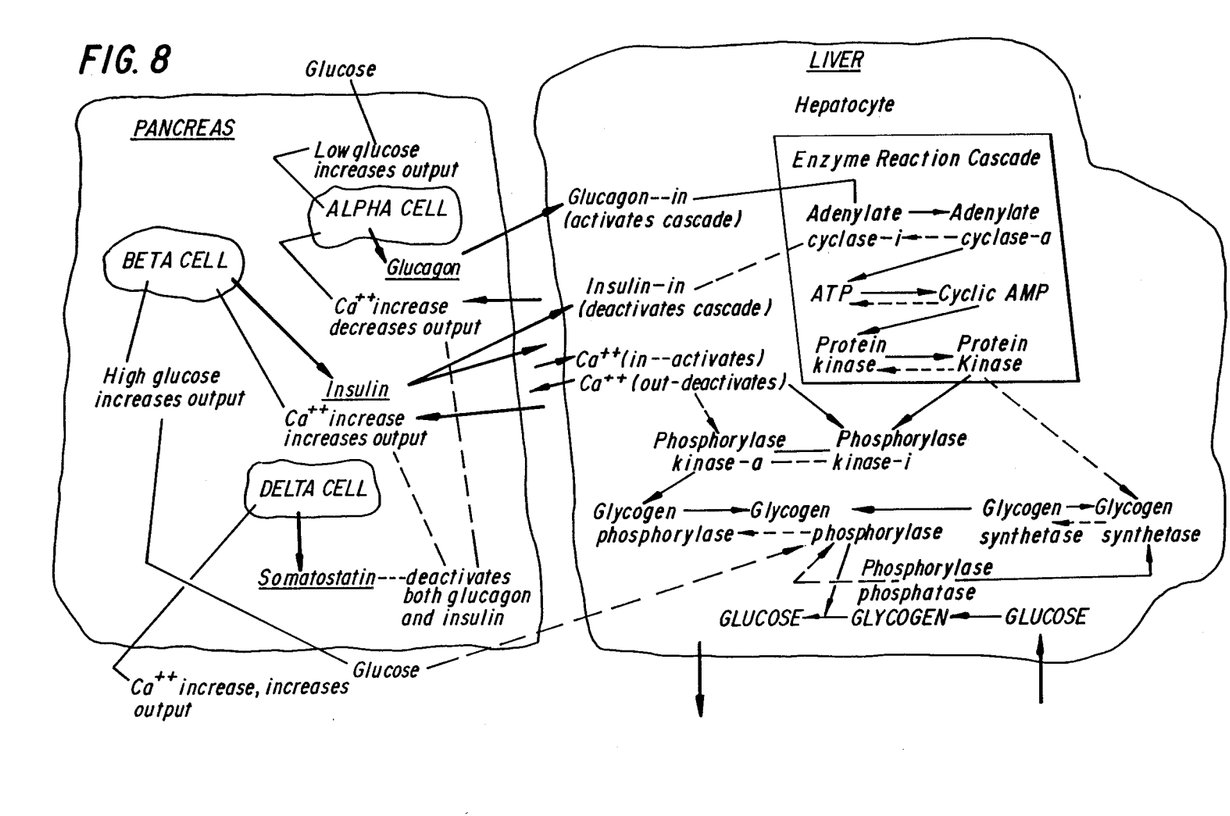
FIG. 8 is a drawing presenting the overall outline of the interaction of pancreatic alpha, beta and delta cells, liver cells and field effects thereon.

FIG. 8 illustrates the interplay between cellular ionic calcium and the key elements controlling blood glucose levels. In the pancreas, alpha cells produce glucagon, which at low glucose levels activates an enzyme reaction cascade in the liver that leads to increased glucose output from stored glycogen. Pancreatic beta cells, on the other hand, produce insulin, which deactivates the liver cascade as well as increases absorption of glucose by most body cells. Somatostatin, produced by pancreatic delta cells deactivates both glucagon and insulin. Calcium ions are required to increase and/or decrease the production of these hormones, as well as to activate phosphorylase kinase in the liver. Thus, timing of the application of exogenous fields to produce optimal effects is tied to blood glucose levels, which in turn are directly related to food intake timing.

EXAMPLE I

Two males having Type II diabetes and having initial blood glucose levels of 243 and 213 mg/dL were used in this study. Both subjects were over 60 years of age and showed evidence of glucose in their urine. Field coil element 2 of FIG. 1 was strapped around the midriff of each subject as shown in FIG. 2(a) and FIG. 2(b) and a resonant frequency electromagnetic field applied daily for about 15 minutes pre-prandially and approximately two hours post-prandially. This treatment was continued for three months, with random breaks to evaluate glucose levels without fields. The conditions of the resonant electromagnetic field were as follows:

| | |
|---|---|
| Frequency | 15 Hz |
| Field Coil Resistance | 175 Ohms |
| Field Dimensions | Approx. 10" × 8" |
| Field Supply Voltage | 117 VAC |
| Pulse Width | 1–2 mSec |

During this period dietary intake of mono- and disaccharides was reduced but not eliminated and general rules for food intake recommended by the American Diabetes Association were followed.

Analysis of blood samples indicated that the resonant frequency electromagnetic fields elevated blood glucose levels when the field was applied before or during meals. Conversely, when the field was applied 1–2 hours after meals, the lowering of glucose levels was noticeably accelerated. Treatment was therefore continued with application of the resonant electromagnetic field only post-prandially, approximately 1½ hours after meals. After a total treatment time of three months, median fasting blood glucose of both subjects had reached approximately 150 mg/dL. At this time, it was noted that resonant fields were no longer significantly reducing fasting blood glucose levels. Further experimentation indicated that post-prandially applied non-resonant fields would further reduce glucose levels if applied immediately after meals. This non-resonant field effect is believed due to improved liver glucose storage caused by such fields, after fasting blood glucose levels are lowered to levels below about 150 mg/dL.

The electromagnetic field was adjusted to a non-resonant field having the following conditions:

| | |
|---|---|
| Frequency | 23–28 Hz |
| Field Coil Resistance | 175 Ohms |
| Field Dimensions | Approx. 10" × 8" |
| Field Supply Voltage | 15 VDC |
| Pulse Width | 1–2 mSec |

Figure 6:
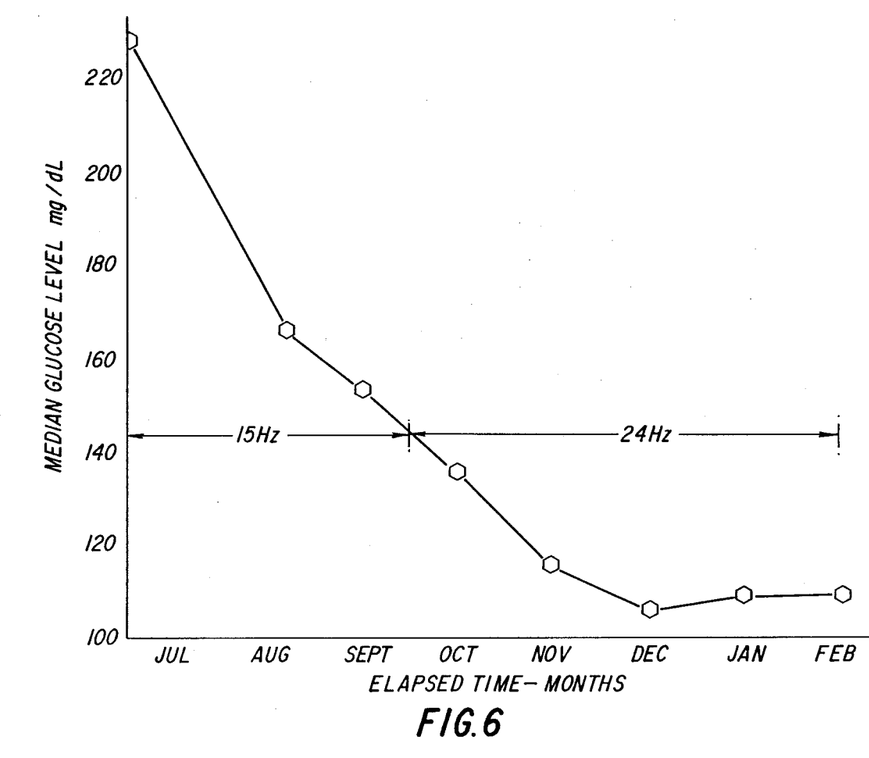
FIG. 6 is a graph showing the effect over eight months of use on test subject of the combination of resonant and non-resonant electromagnetic fields.

The test subjects were then treated with this non-resonant electromagnetic field post-prandially for 1 to 1½ hours daily. After 60 days of treatment with the non-resonant electromagnetic field (again with a few random breaks to evaluate effects with no fields), their fasting blood glucose levels had been reduced to normal values, (i.e., 80–120 mg/dL) in both subjects. FIG. 6 presents eight months of data showing the decline of monthly median blood glucose levels of one of the test subjects. The second test subject at the end of the same period of time was approximately 90 mg/dL.

Neither patient was on any type of diabetes medication during the entire test period. At the completion of the testing period, dietary restrictions were lifted on both patients, with no deleterious effects.

EXAMPLE II

This example is given to show the effects of a resonant frequency electromagnetic field alone on blood glucose levels when fasting blood glucose levels were still excessively elevated.

A test subject received breakfast, lunch and dinner at 7:00 AM, Noon and 5:00 PM, respectively. Shortly after each meal, the test subject was treated with a resonant frequency magnetic field as described in Example I. The blood glucose levels of the test subject were analyzed at various times throughout the day.

As a control, the same test subject was given the same breakfast, lunch and dinner at the same hour a few days prior. Blood glucose levels were similarly determined throughout the day.

Figure 7:
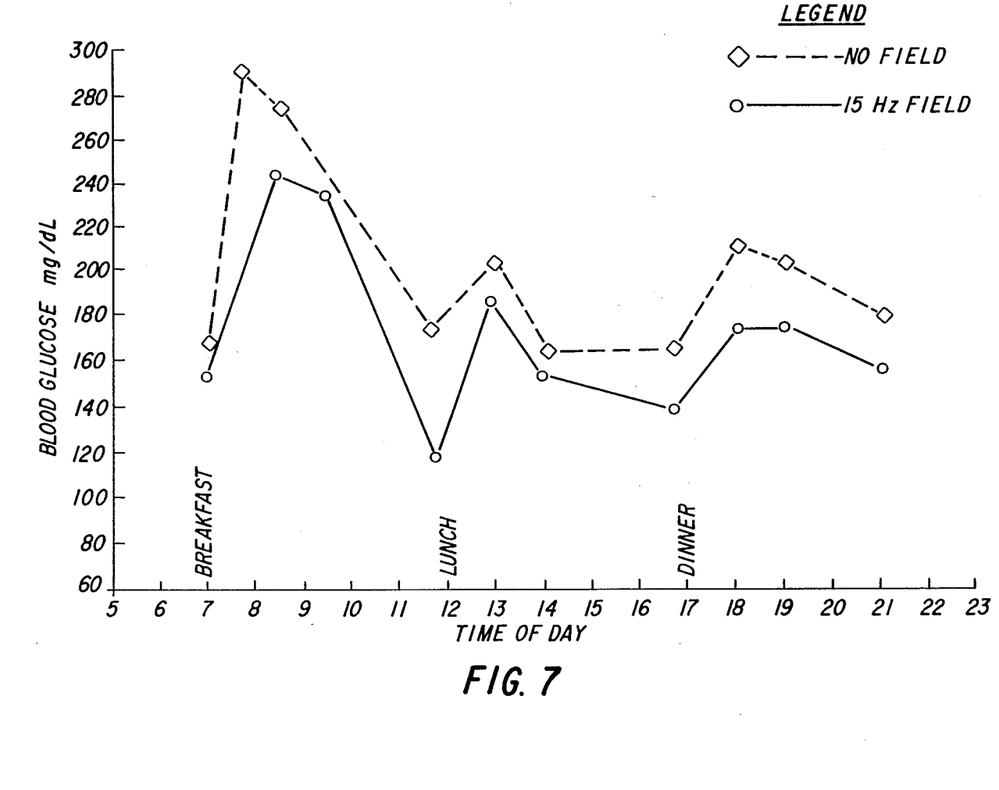
FIG. 7 is a graph showing the effect of the use of a resonant electromagnetic field alone on a patient early in the treatment.

The results are reported in the graph in FIG. 7. As can be seen, in all caes where glucose levels were elevated, a considerable reduction in glucose levels was achieved by the use post-prandially of a resonant frequency electromagnetic field, as compared to glucose levels when eating the same foods without post-prandial application of a field. However, in no instance was a normal glucose level attained.

Thus, while the invention has been described in detail with respect to exemplary embodiments thereof, it will be understood by those of ordinary skill in the art that other variations and modifications may be effected which are within the scope and spirit of the invention.

It is claimed:

1. A method of controlling blood glucose levels in a living animal afflicted with hyperglycemia comprising subjecting at least the liver/pancreas area of said animal defined as having a fasting blood glucose level of at least 180 mg/dL to a resonant frequency electromagnetic field applied post-prandially on a daily basis until the animal's fasting blood glucose level is reduced at least to about 150 mg/dL, then stopping application of said resonant frequency electromagnetic field and subjecting said animal to a non-resonant frequency electromagnetic field to further reduce the animal's blood glucose level.

2. A method according to claim 1 wherein the resonant frequency electromagnetic field has a frequency of 15 Hz plus or minus 0.5 Hz and the non-resonant frequency electromagnetic field has a frequency of 23–28 Hz.

3. A method according to claim 1 wherein the resonant field is applied for about 0.5 to 2 hours.

4. A method according to claim 1 wherein the non-resonant field is applied for 0.5 to 1.5 hours.

5. A method according to claim 1 wherein both the resonant and non-resonant electromagnetic fields are substantially uniform magnetic fields of field strength ranging from 0.1 to 1,000 gauss.

6. A method of controlling cellular influx and efflux of ionic calcium which comprises applying to a secretory cell or cells during the functioning cycle of the cell or cells a resonant frequency field to cause said influx and a non-resonant frequency field to cause said efflux.

7. A method according to claim 6 wherein said cell or cells comprise pancreatic beta cells and wherein the resonant field causes an influx of ionic calcium into pancreatic beta cells to increase their insulin output, while conversely, the non-resonant field causes an efflux of ionic calcium to decrease their insulin output.

8. A method according to claim 6 wherein the resonant field is applied to liver hepatocyte cells and causes an influx of ionic calcium into said liver hepatocytes to activate the enzyme phosphorylase kinase, increasing the conversion of glycogen to glucose, while conversely, the non-resonant field when applied to said liver hepatocytes causes an efflux of ionic calcium from said hepatocytes, deactivating the enzyme phosphorylase kinase, to decrease the conversion of glycogen to glucose.

9. A method according to claim 6 wherein the step of applying the resonant and/or non-resonant fields comprises generating said fields electromagnetically by electric currents in field coils such as Helmholtz coils.

10. A method according to claim 6 wherein the step of applying resonant and non-resonant fields comprises applying vibratory or rotational motion to a permanent magnet.

11. A method according to claim 6 wherein the step of applying resonant and/or non-resonant fields comprises generating appropriately modulated radio frequency power sources.

12. A method according to claim 6 wherein the step of applying resonant and/or non-resonant fields comprises generating appropriately modulated ultrasonic power sources.

13. A method according to claim 7 further comprising measuring blood glucose levels over time, and wherein the resonant field is applied to said cells in vivo blood when glucose levels are elevated and the non-resonant field is applied when blood glucose levels are below normal to bring glucose levels to the normal range.

14. A method according to claim 7 wherein said cells further comprise pancreatic alpha cells and wherein the resonant field causes an influx of ionic calcium into said pancreatic alpha cells to decrease glucagon output, while conversely, the non-resonant field causes an efflux of ionic calcium from said pancreatic alpha cells to increase glucagon output.

15. A method according to claim 14 further comprising measuring blood glucose levels over time, and wherein the resonant field is applied to said cells in vivo when blood glucose levels are elevated and the non-resonant field is applied when blood glucose levels are below normal to bring glucose levels to the normal range.

16. A method according to claim 8 wherein the resonant field is applied when glucose levels are low and the non-resonant field is applied when glucose levels are high to bring glucose levels to normal range.

17. A method of controlling blood glucose levels in a living animal afflicted with hypoglycemia, comprising subjecting at least the liver/pancreas area of an animal defined as having a fasting blood sugar level less than 80 mg/dL to a non-resonant electromagnetic field applied pre-prandially on a daily basis until the animal's blood glucose level is increased to between 80 and 120 mg/dL.

* * * * *